United States Patent [19]

MaClean et al.

[11] Patent Number: 5,079,264
[45] Date of Patent: Jan. 7, 1992

[54] CHEMICAL PROCESS

[75] Inventors: Lachlan MaClean; David L. Roberts, both of Nottinghamshire; Kenneth Barron, Tyne and Wear; Kenneth J. Nichol; Albert E. Harrison, both of Nottinghamshire, all of England

[73] Assignee: The Boots Co. PLC, Nottingham, England

[21] Appl. No.: 663,085

[22] Filed: Mar. 1, 1991

Related U.S. Application Data

[60] Continuation of Ser. No. 577,709, Sep. 4, 1990, abandoned, which is a division of Ser. No. 378,216, Jun. 23, 1989, Pat. No. 5,011,931.

[30] Foreign Application Priority Data

Nov. 18, 1987 [GB] United Kingdom ............... 8726950

[51] Int. Cl.$^5$ .................. A61K 31/165; C07C 233/54
[52] U.S. Cl. .................................... 514/629; 514/312; 546/153; 546/155; 546/156; 564/218
[58] Field of Search .................... 564/218; 514/629

[56] References Cited

U.S. PATENT DOCUMENTS

| | | | |
|---|---|---|---|
| 3,920,699 | 11/1975 | Connor et al. | 260/326.11 |
| 4,192,873 | 3/1980 | Ferrini et al. | 424/246 |
| 4,263,455 | 4/1981 | Ferrini et al. | 564/305 |
| 4,302,460 | 11/1981 | Davies et al. | 424/258/ |
| 4,442,109 | 4/1984 | Davies | 514/312 |
| 4,447,435 | 5/1984 | Davies | 514/312 |
| 4,552,884 | 11/1985 | Sim et al. | 514/312 |
| 4,636,512 | 1/1987 | Clemence et al. | 514/312 |
| 4,772,614 | 9/1988 | Davies | 514/312 |
| 4,877,793 | 10/1989 | Davies et al. | 514/301 |
| 5,011,931 | 4/1991 | Maclean | 546/155 |

FOREIGN PATENT DOCUMENTS

| | | |
|---|---|---|
| 0149519 | 7/1985 | European Pat. Off. |
| 2532939 | 3/1984 | France |
| 1591207 | 6/1981 | United Kingdom |

OTHER PUBLICATIONS von Strandtmann, M., et al., "Heterocyclic Syntheses with B-Ketosulfoxides, etc.", J. Het. Chem., p. 273 (1972).
Maclean, L. et al., "Process for the Synthesis of 3-(methylthio)-4 Quinoline Derivatives, etc.", CA 111, 232593j (1989).
Camps, Chem. Ber., 34, 2703 (1901).
Clemence et al., J. Het. Chem., 21, 1345 (1984).
Yanigisawa et al., Chem. Pharm. Bull., 21, 1080-1089 (1973).
J. K. Landquist, Synthetic Antimalarials, Part XLVI, 1038 (1951).
G. Jones (ed.), Heterocyclic Compounds, 32, 190-197 (1977).
Elderfield, Heterocyclic Compounds, 4, 60-62.
Katritzky, Comprehensive Heterocyclic Chem., 2, 74 (1979).
Merck Index (10th Ed.) Organic Name Reactions Appendix, p. ONR-16 (1983).
Van Leusen et al., Journal of Organic Chemistry, 33, 66-70 (1968).
Connor et al., Journal of Heterocyclic Chemistry, 15, 113-114 (1978).
Oki et al., Bulletin of the Chemical Society of Japan, 44, 828-833 (1971).
PCT Search Report.

Primary Examiner—Glennon H. Hollrah
Assistant Examiner—Susan P. Treanor
Attorney, Agent, or Firm—Armstrong, Nikaido, Marmelstein, Kubovcik & Murray

[57] ABSTRACT

A process to prepare compounds of formula I

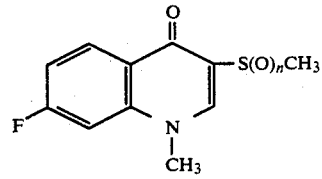

in which n=0, 1 or 2 comprising the cyclization of compounds of formula II

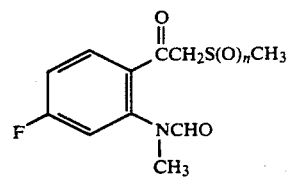

in which n=0, 1 or 2. The cyclization may be effected in the presence of an organic or inorganic base or thermally at a temperature in the range 40°-160° C.

Compounds of formula II and certain analogues thereof are disclosed as cardiovascular agents.

11 Claims, No Drawings

CHEMICAL PROCESS

This application is a continuation of application Ser. No. 577,709 filed Sept. 4, 1990 now abandoned which in turn is divisional of application Ser. No. 378,216, filed June 23, 1989 now U.S. Pat. No. 5,011,931.

This invention relates to a process for the preparation of certain quinolone compounds.

UK Patent 2047691 describes quinolone compounds having therapeutic activity as antihypertensive agents and also describes various processes for their manufacture. EP 149519 also describes some of these quinolone compounds having therapeutic activity in the treatment of heart failure.

UK 2047691 discloses that certain quinolones may be prepared by reacting β-ketosulphoxides of the general formula

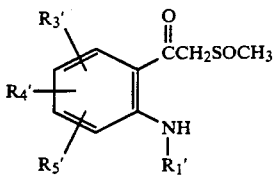

in which $R_1'$ is lower alkyl, with a tri(lower alkyl)-orthoformate.

We have now prepared valuable novel compounds useful in a process to produce some of the quinolones described in UK 2047691. These novel compounds have an inherent property not possessed by the above-described β-ketosulphoxides, namely that they will undergo intramolecular cyclisation to produce said quinolone compounds.

The present invention provides a process to prepare compounds of formula I,

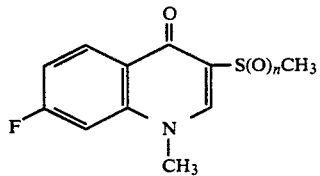

in which n is 0, 1 or 2, comprising the cyclisation of compounds of formula II,

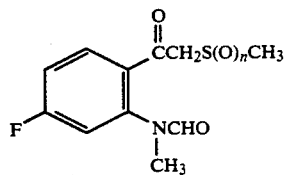

in which n is 0, 1 or 2.

Compounds of formula I have valuable therapeutic activity in the treatment of cardiovascular diseases, especially in the treatment of hypertension and heart failure. A specific compound of formula I provided by a process according to the present invention is 7-fluoro-1-methyl-3-methylthio-4-quinolone. This compound may be oxidised by known methods to give 7-fluoro-1-methyl-3-methylsulphinyl-4-quinolone, (flosequinan), for example by reaction with 3-chloroperoxybenzoic acid (see, for example UK 2047691). Flosequinan has especially valuable therapeutic activity in the treatment of heart failure and hypertension.

It has been found that the yields provided in a process according to the present invention are generally greater than 60%, with preferred processes providing a yield in excess of 80%. The yields are reproducible and are unexpectedly high, particularly in view of the potential for forming side-products, for example by deformylation of compounds of formula II before the cyclisation reaction has been completed.

The cyclisation reaction may be effected in the presence of an organic or inorganic base, for example triethylamine, sodium ethoxide or sodium hydroxide, or by heating the compound of formula II in a suitable liquid, inert to the conditions of the reaction, to a temperature in the range 40°–160° C. The liquid is preferably a solvent for the compound of formula II, e.g. an alcoholic solvent such as isopropyl alcohol, 1-octanol or 2-methoxyethanol.

It has been observed that particular process advantages are obtained in a process according to the invention when n is 1 or 2, especially when n is 2.

Preferably the cyclisation reaction in a basic medium is effected in the presence of an amine or an ion selected from hydroxide ion, alkoxide ion or thiolate ion. Particularly suitable bases useful in the cyclisation reaction are sodium hydroxide, sodium ethoxide, triethylamine and pyridine. Preferably the base is sodium hydroxide in aqueous solution.

The thermal cyclisation of compounds of formula II represents a preferred feature of the invention as particularly valuable yields of the product are obtained. The thermal cyclisation of compounds of formula II to compounds of formula I in which n is 1 or 2 is especially preferred as yields in excess of 95% may be obtained. Advantageously the compounds of formula II are cyclised in separate temperature ranges according to the oxidation state of the compound. When n is 0, the cyclisation reaction is preferably carried out at a temperature in the range 130°–160° C., especially 140°–160° C.; when n is 1 the cyclisation reaction is preferably carried out at a temperature in the range 80°–160° C., especially 120°–140° C.; when n is 2 the cyclisation reaction is preferably carried out at a temperature in the range 40°–160° C., especially 90°–140° C. This reaction is preferably carried out at atmospheric pressure, however higher or lower pressures may also be employed.

Compounds of formula II in which n is 0 may be prepared by reaction of compounds of formula III,

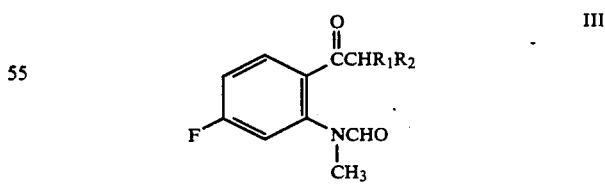

in which $R_1$ represents a leaving group, for example halo, e.g. chloro or bromo and $R_2$ represents hydrogen or $R_1$, with a sulphur nucleophile in the form of a methanethiolate anion. Preferably $R_1$ represents chloro and $R_2$ represents hydrogen.

Compounds of formula II are novel compounds.

In a further preferred feature of the invention the step from a compound of formula III to the compound of formula II in which n is 0 and the step from the compound of formula II in which n is 0 to the compound of formula I in which n is 0 may be effected in one stage by the reaction of a compound of formula III with methanethiolate anion to give the compound of formula I, via the in-situ formation of the compound of formula II. For example, methanolic sodium methanethiolate provides the methanethiolate anion and also acts as a basic medium in which the cyclisation reaction can occur.

Compounds of formula III in which $R_1$ represents halo and $R_2$ represents hydrogen or halo may be prepared by reacting a compound of formula IV,

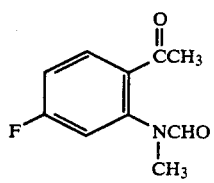

with a halogenating agent, for example, sulphuryl chloride or bromine. A compound of formula III in which $R_2$ represents hydrogen is the dominant product. Other leaving groups $R_1$ may be incorporated into compounds of formula III from the compound of formula IV by methods known in the art.

Compounds of formula III in which $R_1$ represents halo and $R_2$ represents hydrogen or halo are novel compounds.

The compound of formula IV may be prepared by formylating a compound of formula V,

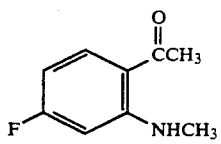

for example, by reaction with formic acetic anhydride.

The compound of formula IV is a novel compound.

The compound of formula V may be prepared by reacting a compound of formula VI,

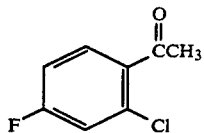

with methylamine, preferably by heating in a sealed vessel in the presence of a catalyst, for example metallic copper.

The compound of formula V is a novel compound.

The compound of formula II in which n is 1 may be prepared by oxidising the compound of formula II in which n is 0. The compound of formula II in which n is 2 may be prepared by oxidizing the compounds of formula II in which n is 0 or 1. The oxidation may be effected, for example, by reaction with 3-chloroperoxybenzoic acid.

Compounds of formula II in which n is 0, 1 or 2 may also be prepared by the formylation of compounds of formula VII,

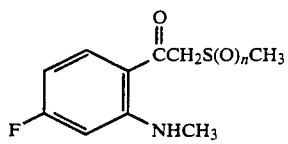

for example, by reaction with formic acetic anhydride

Compounds of formula VII in which n is 1 may be reduced to form the compound of formula V, for example by reaction with zinc powder and acetic acid.

Compounds of formula VII may be prepared by reacting compounds of formula VIII,

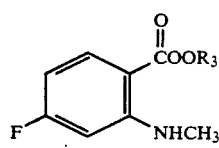

in which $R_3$ represents a $C_{1-4}$ alkyl group, or a compound of formula VIIIa

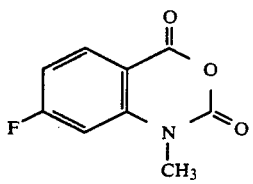

with reagents of formula IX,

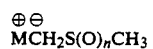

in which n is 0, 1 or 2 and $M^\oplus$ represents an alkali metal cation, for example a sodium or a lithium cation.

Compounds of formula VII in which n is 0 may also be prepared by reacting compounds of formula X,

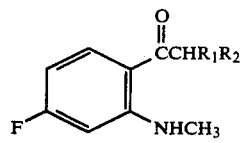

in which $R_1$ represents a leaving group, for example halo, and $R_2$ represents hydrogen, with a sulphur nucleophile in the form of a methanethiolate anion, e.g. by reaction with sodium methanethiolate.

Compounds of formula X may be prepared by deformylating compounds of formula III, for example by heating the compound in a suitable solvent such as 10% aqueous 1,4-dioxan, with a suitable acid catalyst, for example hydrochloric acid.

The compound of formula VII in which n is 1 may be prpared by oxidising the compound of formula VII in which n is 0. The compound of formula VII in which n is 2 may be prepared by oxidizing the compounds of formula VII in which n is 0 or 1. The oxidation may be effected, for example by reaction with 3-chloroperbenzoic acid.

The compound of formula VII in which n is 0 may be prepared by reducing the compound of formula VII in which n is 1, for example by reaction with sodium hydrogen sulphite.

In a preferred aspect of the invention the cyclisation of the compound of formula II in which n is 0 to the compound of formula I in which n is 0 may be incorporated as the last stage in an advantageous 4-stage process. The compound of formula I in which n is 0 may be prepared from the compound of formula V in a sequential process without the isolation of intermediate compounds. It has been found that said 4-stage process, which has been made possible by means of the cyclisation of the compounds of formula II in which n is 0, provides high yields of the compound of formula I in which n is 0. Accordingly, the compound of formula I in which n is 0 may be prepared by:

a) formylating the compound of formula V, for example by reaction with formic acetic anhydride, to give the compound of formula IV;

b) reacting the product of stage (a) with a halogenating agent, for example sulphuryl chloride or bromine to give a compound of formula III in which $R_1$ represents halo, for example chloro or bromo and $R_2$ represents hydrogen, optionally together with compounds of formula III in which $R_1$ and $R_2$ represent halo, for example, chloro or bromo;

c) reacting the product of stage (b) with a sulphur nucleophile in the form of methanethiolate anion, to give the compound of formula II in which n is 0; and d) cyclising the product of stage (c) in the presence of a base to give the compound of formula I.

In an especially preferred process the product of stage (a) is reacted with sulphuryl chloride to give a compound of formula III in which $R_1$ represents chloro and $R_2$ represents hydrogen, and the product of stage (b) is reacted with sodium methanethiolate to give the compound of formula I in which n is 0.

Advantageously the 7-fluoro-1-methyl-3-methylthio-4-quinolone produced in the above-mentioned process is further oxidized to give 7-fluoro-1-methyl-3-methylsulphinyl-4-quinolone (flosequinan), for example by reaction with 3-chloroperoxybenzoic acid.

It is observed that the yield of a compound of formula I obtained using the above-mentioned sequential process (a) to (d) may be very high, typically, in excess of 75%, and especially in excess of 85%. The high overall yield reflects a very favourable yield at each stage of the process. Such a high overall yield is unpredictable in view of the potential for side reactions such as halogenation at other sites, in-situ deformylation of compounds of formulae III and IV and the displacement of the fluorine substituent. The ability to carry out the reaction sequentially is also highly advantageous as it leads to a significant reduction in process time by avoiding the need for isolation and purification of intermediate compounds, thereby also reducing manufacturing cost. In addition, the reactants employed in the above process are readily available and can be handled with ease. Furthermore, the process may be applicable to large scale production.

It can be seen that valuable intermediates of the above-described sequential process are N-formyl compounds having the general formula XI,

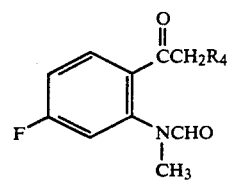

in which $R_4$ is hydrogen, chloro, bromo, methylthio, methylsulphinyl or methylsulphonyl. Compounds of formula XI are believed to be novel.

The novel intermediate compounds of formulae II, III, IV and V also form particularly preferred aspects of the present invention.

Unexpectedly it has been found that the compounds of formula II and certain analogues thereof are useful cardiovascular agents, especially as antihypertensive agents.

In another aspect the present invention provides compounds of formula XII

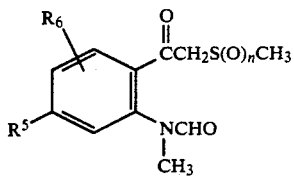

in which $R_5$ and $R_6$, which may be the same or different, each represent hydrogen, a $C_{1-4}$ alkyl group, for example methyl or ethyl, a $C_{1-4}$ alkoxy group, for example methoxy or ethoxy, halo, for example fluoro, chloro or bromo or trifluoromethyl and n is 0, 1 or 2. Preferably $R_6$ is in the 4-position of the benzene ring. More preferably $R_5$ represents hydrogen, halo, methyl, methoxy or trifluoromethyl, especially fluoro or chloro. Particularly preferred compounds are those in which $R_6$ represents hydrogen or methoxy, especially hydrogen. The most preferred group of compounds of formula XII are those represented by formula II hereinbefore described, namely compounds of formula XII in which $R_5$ represents fluoro and $R_6$ represents hydrogen. Preferably n is 1 or 2, especially 1. A particularly valuable compound is 5'-fluoro-N-methyl-2'-(methylsulphinyl)acetylformanilide.

The present invention provides pharmaceutical compositions which comprise a compound of formula XII together with a pharmaceutically acceptable carrier. Specific compounds which may be incorporated in the compositions of this invention are the novel compounds indicated above.

As used hereinafter, the term 'active compound' denotes a formanilide of formula XII. In therapeutic use the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention suitably contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art.

Tablets may be prepared by mixing the active compound with an inert diluent, such as calcium phosphate, in the presence of disintegrating agents, for example maize starch, and lubricating agents, for example magnesium stearate, and tableting the mixture by known methods. Such tablets may if desired be provided with enteric coatings by known methods, for example by the use of cellulose acetate phthalate. Similarly capsules, for example hard or soft gelatin capsules containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1–500 mg of the active compound. Other compositions for oral administration include, for example aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions in aqueous and oily media or sterile solutions in a suitable solvent.

Compositions for topical administration may comprise a matrix in which the active compound is dispersed so that the compound is held in contact with the skin in order to administer the active compound transdermally. Alternatively the active compound may be dispersed in a cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example a $\beta$-blocker such as propranolol, oxprenolol, atenolol or timolol, or a diuretic such as bendrofluazide.

The therapeutic activity of the compounds of formula XII has been demonstrated by means of testing on standard laboratory animals. Such tests include, for example, the oral administration of the compounds to a strain of spontaneously hypertensive rat. Thus the compounds of formula XII are useful for reducing blood pressure in hypertensive mammals. A suitable dose for enteral administration to mammals, including humans, is generally within the range 0.01–25 mg/kg/day, more usually 0.5–10 mg/kg/day given in single or divided doses. For parenteral administration, a suitable dose is generally within the range 0.001–2.5 mg/kg/day, especially 0.005–1 mg/kg/day. Oral administration is preferred.

The compounds are also indicated for use in the treatment of ischaemic heart disease and heart failure in mammals, including humans. Suitable dosages are as hereinbefore stated.

The compounds of formula XII in which $R_5$ represents fluoro and $R_6$ represents hydrogen may be prepared by methods described for the preparation of compounds of formula II. The compounds of formula XII in which $R_5$ represents a substituent other than fluoro may be prepared in a similar manner to the preparation of compounds of formula II using the appropriate starting materials having substituents $R_5$ and $R_6$. For example, compounds of formula XII may be prepared by:

a) oxidising compounds of formula XII in which n is 0 to compounds of formula XII in which n is 1 or 2, or oxidising compounds of formula XII in which n is 0 or 1 to give compounds of formula XII in which n is 2;

b) formylating compounds of formula XIII

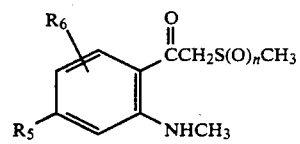

or c) reacting compounds of formula XIV

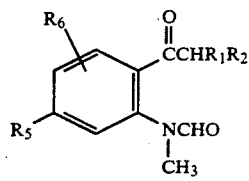

with a sulphur nucleophile in the form of a methanethiolate anion to give compounds of formula XII in which n is 0.

The therapeutic activity of the compounds of the present invention has been demonstrated by the following test which involves the oral administration of the compounds to a strain of spontaneously hypertensive rat. This test was carried out in the following way:

Test

Female rats, weight range 180–240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterialpulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dose reading, blood pressure was measured at 1.5 and 5.0 hours after dosing. A compound was designated as active if it gave a reduction of blood pressure equal to or greater than 9% which is considered to be the minimum significant reduction (p <0.01) on the basis of historical control data.

The compounds of formula XII shown below were active in this test at a dosage of 90 mg/kg or less.

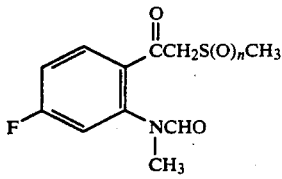

The activity of each compound was found to be:

| n | Active Dose (mg/kg) |
| --- | --- |
| 0 | 30 |
| 1 | 3 |
| 2 | 10 |

The compounds of formula I in which n is 0, 1 or 2 may exist in more than one polymorphic form. The polymorphic forms each have characteristic infra-red spectra and different melting points. In some cases the polymorphic forms are interconvertible, for example the polymorphic form having the lower melting point may be converted to the more thermodynamically stable polymorphic form for example by heating and/or by grinding or during periods of storage.

The invention is illustrated by the following non-limitative Examples, in which parts and percentages are by weight and compositions of mixed solvents are by volume. Characterisation was by elemental analysis and one or more of the following spectroscopic techniques: nuclear magnetic resonance, infra-red and mass spectroscopy. Temperatures are given in degrees Celsius.

EXAMPLE 1

A solution of t-butyl 4-fluoro-2-methylaminobenzoate (28.9 g) in dimethylsulphoxide (133 ml) was added to a solution of potassium t-butoxide (72.2 g) in dimethylsulphoxide (300 ml) at ambient temperature under nitrogen. The stirred mixture was heated at 50° for eight hours and then cooled to ambient temperature. Water (1300 ml) was added to the mixture whilst maintaining the temperature below 35°. Extraction with trichloromethane and evaporation of the extract in vacuo gave 1-(4-fluoro-2-methylaminophenyl)-2-methylsulphinylethanone, m.p. 129°–134°.

EXAMPLE 2

A mixture of 1-(4-fluoro-2-methylaminophenyl)-2-methylsulphinylethanone (100 g), prepared in a similar manner to that described in Example 1, sodium hydrogen sulphite (1 kg) and water (2.5 l) was stirred under nitrogen and heated at 90°–105° for 3 hours. The mixture, was allowed to cool and then stood at ambient temperature for 72 hours. The mixture was extracted with dichloromethane (3×250 ml) and the combined extracts evaporated to give a solid product. Crystallisation from hexane gave 1-(4-fluoro-2-methylaminophenyl)-2-(methylthio)ethanone, m.p. 61.5°–63°.

EXAMPLE 3

A mixture of a solution of methylamine in industrial methylated spirit (33% w/w; 120 ml), industrial methylated spirit (60 ml), 2'-chloro-4'-fluoroacetophenone (51.6 g) and copper powder (0.75 g), was charged to a pressure vessel and heated to 90° for 2 hours. After cooling in an ice bath to 30° the mixture was transferred to a second vessel, heated at 50° and then a solution of sodium sulphide nonahydrate (2.88 g) in water (30 ml) added. The mixture was heated to reflux with stirring for 10 minutes and then filtered. Water (300 ml) was added to the filtrate and the solution heated to reflux. Hydrochloric acid (5M; 90 ml) was added to the hot solution and the mixture heated to reflux for a brief period. The reaction mixture was cooled to ambient temperature and aqueous sodium hydroxide solution (5M; 30 ml) added. The mixture was extracted with dichloromethane (600 ml) and then further extracted with dichloromethane (200 ml). The combined dichloromethane extracts were dried (magnesium sulphate) and evaporated in vacuo to give a crude brown oil. The oil was distilled in vacuo (b.p. 90°, 1 mmHg) to give 4'-fluoro-2'-(methylamino)-acetophenone, m.p. 52°–53°.

EXAMPLE 4

(a) A mixture of acetic anhydride (44 ml) and formic acid (30.0 ml) was stirred and heated to 50°–60° under nitrogen for 2 hours. The mixture was cooled to ambient temperature and 4'-fluoro-2'-(methylamino)-acetophenone (37.8 g), prepared in a similar manner to that described in Example 3, added portionwise over 10 minutes maintaining the temperature below 30°. The reaction mixture was stirred at ambient temperature for 2 hours and then cooled in an ice/salt bath to maintain the temperature below 30° whilst water (160 ml) and aqueous sodium hydroxide solution (specific gravity 1.5; 94 ml) were added sequentially. The mixture was filtered and the layers separated. The aqueous layer was extracted with dichloromethane (2 x 60 ml), and then stored overnight under nitrogen. The dichloromethane solution was stirred under nitrogen in an ice/salt bath and a solution of sulphuryl chloride (40 ml) in dichloromethane (60 ml) added dropwise over 40 minutes whilst maintaining the temperature below 1.5°. After stirring below 0° for 1.75 hours, water (140 ml) was added to the solution over a period of 30 minutes whilst maintaining the temperature below 30°. The layers were separated and the organic phase evaporated in vacuo to give a mixture of 2'-chloroacetyl-5'-fluoro-N-methylformanilide and 2'-dichloroacetyl-5'-fluoro-N-methylformanilide in the form of a red/brown oil.

(b) The mixture from Example 4(a) (47.0 g) was dissolved in a mixture of 1,4-dioxan (270 ml), water (30 ml) and hydrochloric acid (2M; 4.5 ml) and the mixture heated to reflux for 1.75 hours. The mixture was cooled to ambient temperature and evaporated in vacuo. The residue was dissolved in dichloromethane (150 ml), and the solution washed sequentially with saturated aqueous sodium hydrogen carbonate solution (50 ml) and water (30 ml). The dichloromethane was evaporated in vacuo to give a mixture of 2-chloro-1-(4-fluoro-2-methylaminophenyl)ethanone and 2,2-dichloro-1-(4-fluoro-2-methylaminophenyl)ethanone in the form of a green/brown oil which solidified on standing.

(c) The mixture from Example 4(b) (42.4 g) was dissolved in dichloromethane (240 ml) and cooled to 0° in an ice/salt bath under nitrogen. Methanolic sodium methanethiolate solution (2.52M; 180 ml) was added dropwise over a period of 35 minutes whilst maintaining the temperature below 5°. The cooling bath was removed and the stirred mixture allowed to warm to ambient temperature. After 1.5 hours the mixture was acidified with hydrochloric acid (5M; 30 ml) and then diluted with water (120 ml). The layers were separated and the aqueous phase extracted with dichloromethane (100 ml). Evaporation of the combined organic phases in vacuo provided a green/brown oil. Purification by high performance liquid chromatography carried out using a Waters Prep LC/System 500A instrument fitted with one PrepPAK (RTM) 500/silica cartridge and eluting with dichloromethane/petroleum ether (b.p. 60°-80°) (98:2) at 250 ml/min. gave a solid which was crystallised from hexane. The product was washed with hexane and dried at 50° in vacuo to give 1-(4-fluoro-2-methylaminophenyl)-2-(methylthio)ethanone, m.p. 63.5°-64.5°.

EXAMPLE 5

A mixture of acetic anhydride (16.5 ml) and formic acid (11.2 ml) was stirred and heated at 50°-60° under nitrogen for 2 hours. The mixture was cooled to ambient temperature and 1-(4-fluoro-2-methylaminophenyl)-2-(methylthio)ethanone (4.0 g), prepared in a similar manner to that described in Example 4, added over a period of 5 minutes. The mixture was stirred at ambient temperature for 2.75 hours and then cooled in an ice/salt bath to maintain the temperature below 30° whilst, water (50 ml) was added over a period of 30 minutes. The mixture was extracted with dichloromethane (2×25 ml), the organic phases combined, washed with water (2×20 ml) and then evaporated in vacuo to give an oily product. Purification of the oily product by high performance liquid chromatography carried out using a Gilson system fitted with a 2" Dynamax silica column and eluting with dichloromethane/methanol (99:1) at 16 ml/min gave 5'-fluoro-N-methyl-2'-(methylthio)acetylformanilide in the form of a pale yellow oil.

EXAMPLE 6

A solution of 5'-fluoro-N-methyl-2'-(methylthio)-acetylformanilide (0.68 g), prepared in a similar manner to that described in Example 5, in 2-methoxyethanol (30 ml) was heated to reflux. Heating under reflux at 131° was continued for 6 days, after which the mixture was evaporated in vacuo to give a solid product (0.63 g). Crystallisation of a sample of the solid product (0.28 g) from industrial methylated spirit (5 ml) gave 7-fluoro-1-methyl-3-methylthio-4-quinolone, m.p.158.5°-160° (0.08 g).

EXAMPLE 7

A mixture of 5'-fluoro-N-methyl-2'-(methylthio)-acetylformanilide (2.00 g), prepared in a similar manner to that described in Example 5, and aqueous sodium hydroxide solution (1M; 50 ml) was stirred for 2.5 hours at ambient temperature and then filtered. The solid was washed with water (2×10 ml) and then dried at 50° in vacuo to give 7-fluoro-1-methyl-3-methylthio-4-quinolone, m.p.164.5°-165.5° (1.55 g).

EXAMPLE 8

(a) A mixture of acetic anhydride (16.5 ml) and formic acid (11.2 ml) was stirred and heated at 50°-60° under nitrogen for 2 hours. The mixture was cooled to just below 0° and 1-(4-fluoro-2-methylaminophenyl)-2-methylsulphinylethanone (17.2 g), prepared in a similar manner to that described in Example 1, added over a period of 5 minutes. The mixture was stirred at just below 0° for 5 hours and then stored at 4° overnight. The mixture was cooled in an ice/salt bath to maintain the temperature below 0° whilst water (60 ml) was added. The mixture was evaporated in vacuo below 15° to give a green/brown oil. Purification of the oil by high performance liquid chromatography carried out using a Gilson system fitted with a 2" Dynamax silica column and eluting with dichloromethane/methanol (97.5:2.5) at 20 ml/min gave 5'-fluoro-N-methyl-2'-methylsulphinylacetylformanilide in the form of a colourless oil.

(b) A solution of 5'-fluoro-N-methyl-2'-methylsulphinylacetylformanilide (0.77 g) in 2-methoxyethanol (25 ml) was heated to reflux over 20 minutes. Ater heating under reflux at 128° for 45 minutes the mixture was evaporated in vacuo to give 7-fluoro-1-methyl-3-methylsulphinyl-4-quinolone, m.p.225.5°-227° (0.69 g).

EXAMPLE 9

A mixture of 5'-fluoro-N-methyl-2'-methylsulphinylacetylformanilide (1.99 g), prepared in a similar manner to that described in Example 8, and aqueous sodium hydroxide solution (1M; 50 ml) was stirred for 2 hours at ambient temperature and then filtered. The solid was washed with water (2×10 ml) and then toluene (2×10 ml). The solid was dried at 50° in vacuo to give 7-fluoro-1-methyl-3-methylsulphinyl-4-quinolone, m.p.228.5°-230° (1.55 g).

EXAMPLE 10

A mixture of acetic anhydride (66.0 ml) and formic acid (45.0 ml) was stirred and heated at 50°-60° under nitrogen for 2 hours and then cooled to ambient temperature. 1-(4-Fluoro-2-methylaminophenyl)-2-methylsulphinylethanone (69.0 g), prepared in a similar manner to that described in Example 1, was added slowly below 30° and the mixture stirred for a further 2 hours. The mixture was cooled in an ice/salt bath to 0° and water (500 ml) added whilst maintaining the temperature below 30°. The mixture was filtered and the filtrate cooled in an ice/salt bath to 0°. Toluene (100 ml) and aqueous sodium hydroxide solution (specific gravity 1.5; 140 ml) were added sequentially, again maintaining the temperature below 30°. The mixture was stirred for 30 minutes at ambient temperature and the product collected by filtration, washed with water (200 ml), toluene (3×50 ml) and hexane (2×50 ml) and then dried at 50° in vacuo to give 7-fluoro-1-methyl-3-methylsulphinyl-4-quinolone, m.p.228.5°-230.5° (53.7 g).

EXAMPLE 11

(a) A solution of 3-chloroperoxybenzoic acid (8.29 g) in dichloromethane (200 ml) was added to a solution of 1-(4-fluoro-2-methylaminophenyl)-2-methylsulphinylethanone (10.0 g), prepared in a similar manner to that described in Example 1, in dichloromethane (175 ml) over a period of 7 minutes whilst maintaining the temperature below 30°. The mixture was stirred at ambient temperature for 2 hours, saturated aqueous sodium hydrogen carbonate solution (244 ml) was added and the mixture stirred at ambient temperature for a further 2 hours. The dichloromethane layer was isolated and the aqueous layer extracted with dichloromethane (2×60 ml). The organic phases were combined, dried (magnesium sulphate) and evaporated in vacuo to give a solid which was crystallised from acetone to give 1-(4-fluoro- 2-methylaminophenyl)-2-methylsulphonylethanone, m.p. 143.5°–145°.

(b) A mixture of acetic anhydride (19.8 ml) and formic acid (13.5 ml) was stirred and heated at 60° under nitrogen for 2 hours. 1-(4-Fluoro-2-methylaminophenyl)-2-methylsulphonylethanone (10.0 g), was added portionwise to the mixture at ambient temperature with stirring. The mixture was stirred at 30° for 30 minutes. Water (30 ml) was added to the reaction mixture which was then stirred at 30° for 30 minutes. Concentration of the reaction mixture by evaporation in vacuo gave a green oil. The oil was dissolved in trichloromethane (50 ml) and washed with aqueous sodium hydrogen carbonate solution (7% w/w; 2×30 ml). The trichloromethane extract was dried (magnesium sulphate) and evaporated in vacuo to give a green oil which solidified at ambient temperature. Recrystallisation from toluene gave 5'-fluoro-N-methyl-2'-methylsulphonylacetylformanilide, m.p. 94.5°–95.5°.

(c) A solution of 5'-fluoro-N-methyl-2'-methylsulphonylacetylformanilide (0.40 g) in 2-methoxyethanol (15 ml) was heated at 40° for 5 days. The mixture was allowed to cool to ambient temperature and then evaporated in vacuo to give a solid (0.43 g). Crystallisation from industrial methylated spirit (28 ml) gave 7-fluoro-1-methyl-3-methylsulphonyl-4-quinolone, m.p. 225°–226° (0.21 g). Evaporation of the filtrate in vacuo and crystallisation of the residual solid from industrial methylated spirit (15 ml) gave further 7-fluoro-1-methyl-3-methylsulphonyl-4-quinolone, m.p. 224°–225° (0.03 g). The products were combined and heated at 90° with grinding to give 7-fluoro-1-methyl-3-methylsulphonyl-4-quinolone, m.p. 236°–237° (0.24 g).

EXAMPLE 12

A solution of 5'-fluoro-N-methyl-2'-methylsulphonylacetylformanilide (0.20 g), prepared in a similar manner to that described in Example 11, in 2-methoxyethanol (25 ml) was heated at 79° for 5.5 hours. The mixture was allowed to cool to ambient temperature and then evaporated in vacuo to give a solid (0.21 g). Recrystallisation of a sample of the solid (0.10 g) from industrial methylated spirit (7 ml), gave 7-fluoro-1-methyl-3-methylsulphonyl-4-quinolone, m.p.224°–225° (0.08 g). The product was heated at 90° with grinding to give 7-fluoro-1-methyl-3-methylsulphonyl-4-quinolone, m.p.235°–236° (0.08 g).

EXAMPLE 13

A solution of 5'-fluoro-N-methyl-2'-methylsulphonylacetylformanilide (1.0 g), prepared in a similar manner to that described in Example 11, in isopropyl alcohol (20 ml) was heated to reflux for 3.5 hours. The mixture was cooled to ambient temperature and the product collected by filtration and dried in vacuo at 50° to give 7-fluoro-1-methyl-3-methylsulphonyl-4-quinolone, m.p. 234.5°–235° (0.6 g).

EXAMPLE 14

A solution of 5'-fluoro-N-methyl-2'-methylsulphonylacetylformanilide (0.20 g), prepared in a similar manner to that described in Example 11, in 2-methoxyethanol (25 ml) was heated at 97° for 5.3 hours. The mixture was allowed to cool to ambient temperature and then evaporated in vacuo to give 7-fluoro-1-methyl-3-methylsulphonyl-4-quinolone, m.p. 234°–235° (0.19 g).

EXAMPLE 15

A solution of 5'-fluoro-N-methyl-2'-methylsulphonylacetylformanilide (0.20 g), prepared in a similar manner to that described in Example 11, in 2-methoxyethanol (25 ml) was heated to reflux. Heating under reflux at 127° was continued for 2 hours. The mixture was allowed to cool to ambient temperature and then evaporated in vacuo to give 7-fluoro-1-methyl-3-methylsulphonyl-4-quinolone, m.p. 233.5°–235° (0.19 g).

EXAMPLE 16

5'-Fluoro-N-methyl-2'-methylsulphonylacetylformanilide (0.20 g), prepared in a similar manner to that described in Example 11, was added to 1-octanol (25 ml) pre-heated to 160°. The mixture was heated at this temperature for 40 minutes and then allowed to cool to ambient temperature. The mixture was filtered, the solid washed with hexane (2×10 ml) and dried at 50° in vacuo to give 7-fluoro-1-methyl-3-methylsulphonyl-4-quinolone, m.p. 222.5°–224° (0.16 g). The product was heated at 90° with grinding to give 7-fluoro-1-methyl-3-methylsulphonyl-4-quinolone, m.p.234°–235° (0.16 g).

EXAMPLE 17

A mixture of 5'-fluoro-N-methyl-2'-methylsulphonylacetylformanilide (1.50 g), prepared in a similar manner to that described in Example 11, and aqueous sodium hydroxide solution (1M; 40 ml) was stirred for 2 hours. The mixture was filtered, the solid washed with water (2×10 ml) and then dried in vacuo to give 7-fluoro-1-methyl-3-methylsulphonyl-4-quinolone, m.p.234°–235° (1.19 g).

EXAMPLE 18

A mixture of 5'-fluoro-N-methyl-2'-methylsulphonylacetylformanilide (5.0 g), prepared in a similar manner to that described in Example 11, water (50 ml) and isopropyl alcohol (50 ml) was heated to 50°. Aqueous sodium hydroxide solution (1 M; 3 ml) was added and the mixture heated under reflux for 2.5 hours. The mixture was cooled in an ice bath and the product isolated by filtration, washed with water (10 ml), and then isopropyl alcohol (10 ml) to give the crude product (3.3 g). A sample of the crude product (2.0 g) was crystallised from industrial methylated spirit (112 ml) to give 7-fluoro-1-methyl-3-methylsulphonyl-4-quinolone, m.p 221.5°–223° (1.7 g). The product was heated at 90° with grinding to give 7-fluoro-1-methyl-3-methylsulphonyl-4-quinolone, m.p. 235°–236° (1.7 g).

EXAMPLE 19

A solution of sodium ethoxide in ethanol, prepared from sodium metal (2.3 g) and absolute ethanol (50 ml), was added dropwise over 5 minutes to a solution of 5'-fluoro-N-methyl-2'-methylsulphonylacetylformanilide (2.7 g), prepared in a similar manner to that described in Example 11, in absolute ethanol (10 ml) at ambient temperature. The mixture was stirred at this temperature for 30 minutes then added to hydrochloric acid (1M; 100 ml), keeping the temperature below 30°. The mixture was extracted with dichloromethane (2×150 ml). The extracts were combined, dried (magnesium sulphate) and evaporated in vacuo to give the crude product (2.5 g). The crude product was crystallised from industrial methylated spirit to give 7-fluoro-1-methyl-3-methylsulphonyl-4-quinolone, m.p. 221°–222.5° (2.0 g). The product was heated to 90° with grinding to give 7-fluoro-1-methyl-3-methylsulphonyl-4-quinolone, m.p. 234°-235° (2.0 g).

EXAMPLE 20

A mixture of 5'-fluoro-N-methyl-2'-methylsulphonylacetylformanilide (0.20 g), prepared in a similar manner to that described in Example 11, and triethylamine (20 ml) was stirred at ambient temperature for 2.5 hours. Hexane (30 ml) was added to the mixture. The solid product collected by filtration of the mixture was washed with hexane (2×5 ml) and dried at 50° in vacuo to give 7-fluoro-1-methyl-3-methylsulphonyl-4-quinolone, m.p. 233°-234.5° (0.16 g).

EXAMPLE 21

A solution of 5'-fluoro-N-methyl-2'-methylsulphonylacetylformanilide (0.85 g), prepared in a similar manner to that described in Example 11, in pyridine (85 ml) was stirred at ambient temperature for 3 days. The mixture was added to hexane (180 ml) and the solid collected by filtration was dried at 50° in vacuo to give 7-fluoro-1-methyl-3-methylsulphonyl-4-quinolone, m.p.234°-235° (0.49 g).

EXAMPLE 22

(a) A solution of 1-(4-fluoro-2-methylaminophenyl)-2-methylsulphinylethanone (161.0 g), prepared in a similar manner to that described in Example 1, in acetic acid (770 ml) was added to a stirred mixture of zinc dust (228.2 g), acetic acid (210 ml) and ethanol (392 ml) at 80° over 1 hour. The mixture was stirred at 80° for a further 2 hours and then allowed to cool to ambient temperature. The combined filtrates obtained after filtration and washing the residue with dichloromethane (400 ml) were concentrated by distillation until the temperature of the remaining mixture reached 132° and then cooled to ambient temperature. Water (1 l) and dichloromethane (330 ml) were added sequentially, the mixture stirred for 10 minutes and the layers then separated. The aqueous phase was extracted with further dichloromethane (2×200 ml), the organic extracts combined, then washed with aqueous sodium hydroxide solution (5M; 200 ml) and evaporated in vacuo. Distillation in vacuo (b.p. 74°, 0.4 mm Hg) of the residue gave 4'-fluoro-2'-(methylamino)acetophenone, m.p. 52°-53°.

(b) A mixture of acetic anhydride (63 ml) and formic acid (43 ml) was stirred and heated at 50°-60° under nitrogen for 2 hours. The mixture was cooled in an ice/water bath and 4'-fluoro-2'-(methylamino)-acetophenone (52.9 g) added portionwise over 30 minutes, maintaining the temperature below 30°. The reaction mixture was stirred at ambient temperature for 1 hour and then cooled in an ice/salt bath. Water (220 ml) and aqueous sodium hydroxide solution (specific gavity 1.5; 123.5 ml) were then added sequentially, maintaining the temperature below 30°. The mixture was extracted with dichloromethane (3×85 ml) and the combined extracts stored overnight at 0° under nitrogen. The combined extracts were stirred at 0° under nitrogen and a solution of sulphuryl chloride (56 ml) in dichloromethane (75 ml) added over 40 minutes whilst maintaining the temperature below 2°. After stirring at 0° for 2 hours, water (190 ml) was added over 30 minutes whilst maintaining the temperature below 25°. The layers were then separated and the organic phase cooled to 0° in an ice/salt bath. Methanolic sodium methanethiolate solution (2.68M; 266 ml) was added dropwise over 1 hour whilst maintaining the temperature below 5°. The mixture was allowed to warm to ambient temperature, stirred for a further 2 hours, and then hydrochloric acid (5M; 68.5 ml) and water (135 ml) were added sequentially. The layers were separated, the aqueous phase extracted with dichloromethane (50 ml) and the organic phases combined. The solvent was removed from the combined phases by distillation at atmospheric pressure under nitrogen. As the distillation progressed, petroleum ether (b.p. 102°-120°; 205 ml) was added to the flask. Distillation was continued until the mixture reached a temperature of 100°. The mixture was cooled to 20°, filtered and the residue washed with petroleum ether (b.p.102°-120°; 2×50 ml). The solid was dried at 50° in vacuo to give 7-fluoro-1-methyl-3-methylthio-4-quinolone, m.p. 147°-149° (61.3 g).

EXAMPLE 23

(a) A mixture of a solution of methylamine in industrial methylated spirit (33% w/w; 315.8 ml), industrial methylated spirit (291.6 ml), 2'-chloro-4'-fluoroacetophenone (203.4 g) and copper powder (2.8 g) was heated to 80° in a glass autoclave over a period of 1 hour. The mixture was stirred at 80° for a further 2 hours and then allowed to cool to 45° over a period of 1 hour. The mixture was transferred to a second vessel and the autoclave rinsed with industrial methylated spirit (50 ml) which was then added to the second vessel. The mixture was heated to 50°. A solution of sodium sulphide nonahydrate (11.2 g) in water (117 ml) was added and the mixture was heated at 50° for a further 15 minutes. The mixture was filtered and the residue washed with industrial methylated spirit (100 ml). The filtrate and washings were combined and evaporated to give a brown oil. The brown oil was stirred with hydrochloric acid (5M; 800 ml) for 2.5 hours and then dichloromethane (600 ml) added. The layers were separated and the aqueous phase further extracted with dichloromethane (2×300 ml). The organic phases were combined and evaporated to give 4'-fluoro-2'-(methylamino)-acetophenone as a brown oil which solidified at ambient temperature.

b) A mixture of acetic anhydride (92 ml) and formic acid (62.7 ml) was stirred and heated at 50°-60° under nitrogen for 2 hours and then cooled to ambient temperature. A portion of the product from Example 23(a) (77.1 g) was added portionwise over a period of 30 minutes maintaining the temperature below 30°. The reaction mixture was stirred at ambient temperature for 1 hour and then cooled in an ice/salt bath. Water (320 ml) and aqueous sodium hydroxide solution (specific gravity 1.5; 180 ml) were then added sequentially maintaining the temperature below 30°. The mixture was extracted with dichloromethane (3×125 ml) and the combined extracts stored overnight at 0° under nitrogen. The dichloromethane solution was stirred under nitrogen in an ice/salt bath and a solution of sulphuryl chloride (81.7 ml) in dichloromethane (110 ml) added over 35 minutes whilst maintaining the temperature below 0°. After stirring at 0° for 1.75 hours, water (280 ml) was added over a period of 25 minutes whilst maintaining the temperature below 25°. The layers were then separated and the organic phase cooled in an ice/salt bath under nitrogen. A solution of sodium methanethiolate in methanol (2.65 M; 388 ml) was added dropwise over 70 minutes whilst maintaining the temperature below 5°. The mixture was allowed to warm to ambient temperature, stirred for 1.5 hours, acidified with hydrochloric acid (5M; 100 ml) and then kept overnight. Water (200 ml) was added, the layers were separated, the aqueous phase extracted with further dichloromethane (70 ml) and the organic phases combined. The solvent was removed from the combined phases by distillation and replaced by petroleum ether (b.p. 102°–120°; 300 ml) as the distillation progressed. Distillation was continued until the temperature of the remaining mixture reached 100°. The mixture was cooled to 20°, filtered and the residue washed with petroleum ether (b.p. 102°–120°; 2×70 ml). The residue was dried at 50° in vacuo to give an orange-yellow solid (72.9 g). Crystallisation of a sample of the product (0.38 g) from industrial methylated spirit (3.5 ml) gave 7-fluoro-1-methyl-3-methylthio-4- quinolone, m.p. 162°–163° (0.26 g).

EXAMPLE 24

A solution of 5'-fluoro-N-methyl-2'-(methylthio)-acetylformanilide (7.2 g), prepared in a similar manner to that described in Example 5, in dichloromethane (100 ml) was stirred in an ice bath. A solution of 3-chloroperoxybenzoic acid (10.9 g) in dichloromethane (240 ml) was added over 30 minutes maintaining the temperature below 30°. The mixture was stirred at this temperature overnight and then washed with saturated aqueous sodium hydrogen carbonate solution (3×100 ml) and water (2×50 ml). Evaporation in vacuo gave an oily solid which was then crystallised from toluene/hexane to give 5'-fluoro-N-methyl-2'-methylsulphonylacetylformanilide, m.p. 96°–98°.

EXAMPLE 25

3-Chloroperoxybenzoic acid (0.63 g) was added to a solution of 5'-fluoro-N-methyl-2'-methylsulphinylacetylformanilide (0.78 g), prepared in a similar manner to that described in Example 8, in dichloromethane (25 ml). The mixture was stirred at ambient temperature for 2 hours and then washed with saturated aqueous sodium hydrogen carbonate solution (2×20 ml) and water (2×20 ml). Evaporation in vacuo gave an oil which was crystallised from toluene gave to give 5'-fluoro-N-methyl-2'-methylsulphonylacetylformanilide, m.p. 95°–97° C.

EXAMPLE 26

A solution of 3-chloroperoxybenzoic acid (3.49 g) in dichloromethane (80 ml) was added to a stirred solution of 1-(4-fluoro-2-methylaminophenyl)-2-(methylthio)ethanone (4.3 g), prepared in a similar manner to that described in Example 2, in dichloromethane (75 ml) under nitrogen over 15 minutes whilst maintaining the temperature below 25°. The mixture was stirred for a further 2 hours at ambient temperature. The solution was washed with saturated aqueous sodium hydrogen carbonate solution (3×50 ml) and evaporated in vacuo to give a solid product. Crystallisation from toluene gave 1-(4-fluoro-2-methylaminophenyl)-2-methylsulphinylethanone, m.p. 137°–138°.

EXAMPLE 27

A solution of 3-chloroperoxybenzoic acid (7.2 g) in dichloromethane (160 ml) was added over 20 minutes to a stirred solution of 1-(4-fluoro-2-methylaminophenyl)-2-(methylthio)ethanone (4.3 g), prepared in a similar manner to that described in Example 2, in dichloromethane (75 ml) whilst maintaining the temperature below 30°. The mixture was stirred at ambient temperature for 4 hours. The solution was washed with saturated aqueous sodium hydrogen carbonate solution (3×50 ml) and water (2×50 ml) and then evaporated in vacuo to give a solid product. Crystallisation from ethyl acetate gave 1-(4-fluoro-2-methylaminophenyl)-2-methylsulphonylethanone, m.p. 143°–144.5°.

EXAMPLE 28 a) 7-chloro-6-methoxy-3,1-1H-benzoxazine-2,4-dione (57 g) is dissolved in dry N,N-dimethylformamide (250 ml) at ambient temperature and stirred with anhydrous sodium carbonate (27.5 g). Iodomethane (13.8 ml) is added dropwise over a period of ten minutes and the reaction mixture is stirred overnight. The resultant mixture is poured into water (700 ml), allowed to stand overnight and the solid is collected by filtration to give 7-chloro-6-methoxy-1-methyl-3,1-1H-benzoxazine-2,4-dione, m.p. 111°–113°.

b) A mixture of dimethyl sulphoxide (163 ml), toluene (380 ml) and 50% w/w dispersion of sodium hydride in mineral oil (15 g) is heated under nitrogen at 75° for 45 minutes, then cooled to 35° to form dimethyl sulphoxide anion, sodium salt. The resulting suspension is stirred at ambient temperature under nitrogen and the 1-methyl-substituted benzoxazine-2,4-dione (37 g) from a) above is added portionwise. The resulting solution is stirred at room temperature for 1 hour and poured onto ice (500 g). The resultant solution is acidified, neutralised and extracted into dichloromethane (3×200 ml). The combined organic extracts are washed with water, dried over magnesium sulphate and filtered and the solvent is removed by distillation to give 4'-chloro-5'-methoxy-2'-methylamino-2-(methylsulphinyl)acetophenone in the form of an oil.

c) The acetophenone from b) above is reacted with a mixture of acetic anhydride and formic acid in a similar manner to that described in Example 8(a) to give 5'-chloro-4'-methoxy-N-methyl-2'-(methylsulphinylacetyl)formanilide.

EXAMPLE 29

In a similar way to that described in Example 28 (c), the appropriate acetophenones are formylated to give the following compounds (a)–(e)

(a) 4'-chloro-N-methyl-2'-(methylsulphinylacetyl)-formanilide;

(b) 4'-trifluoromethyl-N-methyl-2'-(methylsulphinylacetyl)formanilide;

(c) 4',5'-dimethoxy-N-methyl-2'-(methylsulphinylacetyl)formanilide;

(d) N-methyl-2'-(methylsulphinylacetyl)formanilide; and (e) 4'-methyl-N-methyl-2'-(methylsulphinylacetyl)-formanilide.

The required substituted acetophenones for the above reactions (a), (b), (c), (d) and (e) are prepared in a similar way to that described in Example 28. The appropriate known 1-unsubstituted benzoxazine is converted to the 1-methyl-substituted benzoxazine XV which is then converted to the acetophenone:

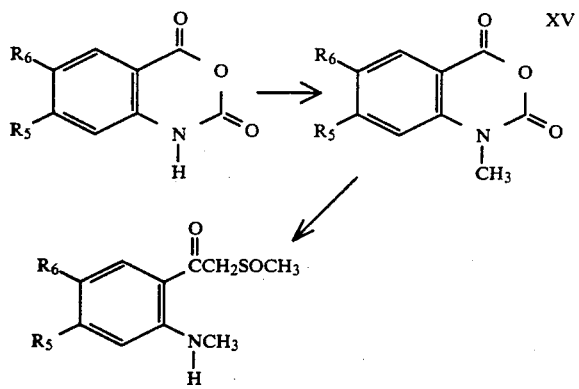

In this way the following intermediates are prepared:

| $R_5$ | $R_6$ | XV m.p.° |
| --- | --- | --- |
| Cl | H | 217-219 |
| $CF_3$ | H | 116-118 |
| $OCH_3$ | $OCH_3$ | 222-225 |
| H | H | * |
| $CH_3$ | H | 169-175 |

*known compound

EXAMPLE 30

In a similar manner to that described in Example 25, the compound 5'-chloro-4'-methoxy-N-methyl-2'-(methylsulphinylacetyl)formanilide of Example 28c) is oxidised to give 5'-chloro-4'-methoxy-N-methyl-2'-(methylsulphonylacetyl)formanilide.

EXAMPLE 31 a) In a similar manner to that described in Example 2, the compound 4'-chloro-5'-methoxy-2'-methylamino-2-(methylsulphinyl)acetophenone of Example 28b) is reduced to give 4'-chloro-5'-methoxy-2'-methylamino-2-(methylthio)acetophenone.

b) In a similar manner to that described in Example 28c) the acetophenone from a) above is formylated to give 5'-chloro-4'-methoxy-N-methyl-2'-(methylthioacetyl)formanilide.

EXAMPLE 32 a) In a similar manner to that described in Example 26 or Example 27, the compound 4'-chloro-5'-methoxy-2'-methylamino-2-(methylthio)acetophenone of Example 31b) is oxidised to 4'-chloro-5'-methoxy-2'-methylamino-2-(methylsulphinyl)acetophenone or 4'-chloro-5'-methoxy-2'-methylamino-2-(methylsulphonyl)acetophenone respectively.

b) Each of the compounds from a) above are formylated in a similar manner to that described in Example 28c) to give 5'-chloro-4'-methoxy-N-methyl-2'-(methylsulphinylacetyl)formanilide or 5'-chloro-4'-methoxy-N-methyl-2'-(methylsulphonylacetyl)formanilide respectively.

We claim:

1. A compound of formula XII

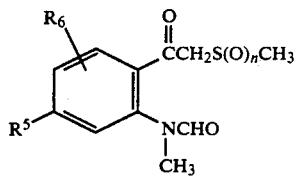

in which $R_5$ and $R_6$, which may be the same or different, each represent hydrogen, a $C_{1-4}$ alkyl group, a $C_{1-4}$ alkoxy group, halo, or trifluoromethyl and n is 0, 1 or 2.

2. A compound according to claim 1 wherein $R_5$ represents fluoro, $R_6$ represents hydrogen and n is 0, 1 or 2.

3. The compound according to either one of claims 1 or 2 which is 5'-fluoro-N-methyl-2'-(methylsulphinyl)acetylformanilide.

4. A pharmaceutical composition comprising a compound of formula XII according to either one of claims 1 or 2 together with a pharmaceutically acceptable carrier.

5. A composition according to claim 4 comprising 5'-fluoro-N-methyl-2'-(methylsulphinyl)acetylformanilide.

6. A composition according to claim 4 in unit dosage form.

7. A composition according to claim 4 wherein the unit dosage of active ingredient is 1-500 mg.

8. A composition according to claim 4 in the form of tablets, capsules or suppositories.

9. A compound of formula XII according to either one of claims 1 or 2 for use as an antihypertensive agent.

10. A method of treating hypertension comprising administering to a hypertensive mammal in need thereof an antihypertensively effective amount of a compound of formula XII according to either one of claims 1 or 2.

11. A method according to claim 10 wherein the compound is 5'-fluoro-N-methyl-2'-(methylsulphinyl)acetylformanilide.

* * * * *